US010768160B2

(12) United States Patent
    Siegel

(10) Patent No.: US 10,768,160 B2
(45) Date of Patent: Sep. 8, 2020

(54) ARTIFICIAL GUT SIMULATOR AND METHOD

(71) Applicant: Regents of the University of Minnesota, Minneapolis, MN (US)

(72) Inventor: Ronald A. Siegel, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 306 days.

(21) Appl. No.: 15/870,263

(22) Filed: Jan. 12, 2018

(65) Prior Publication Data

US 2018/0202987 A1    Jul. 19, 2018

Related U.S. Application Data

(60) Provisional application No. 62/445,477, filed on Jan. 12, 2017.

(51) Int. Cl.
    *G01N 33/15*    (2006.01)
    *G01N 13/00*    (2006.01)

(52) U.S. Cl.
    CPC ............ *G01N 33/15* (2013.01); *G01N 13/00* (2013.01); *G01N 2013/006* (2013.01)

(58) Field of Classification Search
    CPC ... G01N 33/15; G01N 13/00; G01N 2013/006
    USPC .......................................... 73/865
    See application file for complete search history.

(56) References Cited

U.S. PATENT DOCUMENTS

| | | | | |
|---|---|---|---|---|
| 5,468,961 | A * | 11/1995 | Gradon | A61M 16/16 250/343 |
| 7,146,979 | B2 * | 12/2006 | Seakins | A61M 16/0003 128/203.17 |
| 2010/0288024 | A1 * | 11/2010 | Sugiyama | B01D 19/0036 73/61.52 |
| 2013/0019687 | A1 * | 1/2013 | Wosnitza | G01L 19/0654 73/700 |
| 2016/0234904 | A1 * | 8/2016 | Nagai | G01N 21/33 |

* cited by examiner

*Primary Examiner* — Tarun Sinha
(74) *Attorney, Agent, or Firm* — Schwegman Lundberg & Woessner, P.A.

(57) ABSTRACT

An artificial gut simulator and methods are shown. In one example, the artificial gut simulator and methods provide accurate dissolution data by removing detected test sample material from the tester over time.

17 Claims, 2 Drawing Sheets

ARTIFICIAL GUT SIMULATOR AND METHOD

RELATED APPLICATIONS

This patent application claims the benefit of priority, under 35 U.S.C. § 119(e), to U.S. Provisional Patent Application Ser. No. 62/445,477, filed on Jan. 12, 2017, which is incorporated herein by reference in its entirety.

TECHNICAL FIELD

This invention relates to testing devices and methods to simulate a digestive gut. In one example, this invention relates to devices and methods to simulate a digestive gut to evaluate drug delivery.

BACKGROUND

Testing devices and methods are desired to more effectively evaluate efficacy of drug delivery.

DETAILED DESCRIPTION

Figure 1:
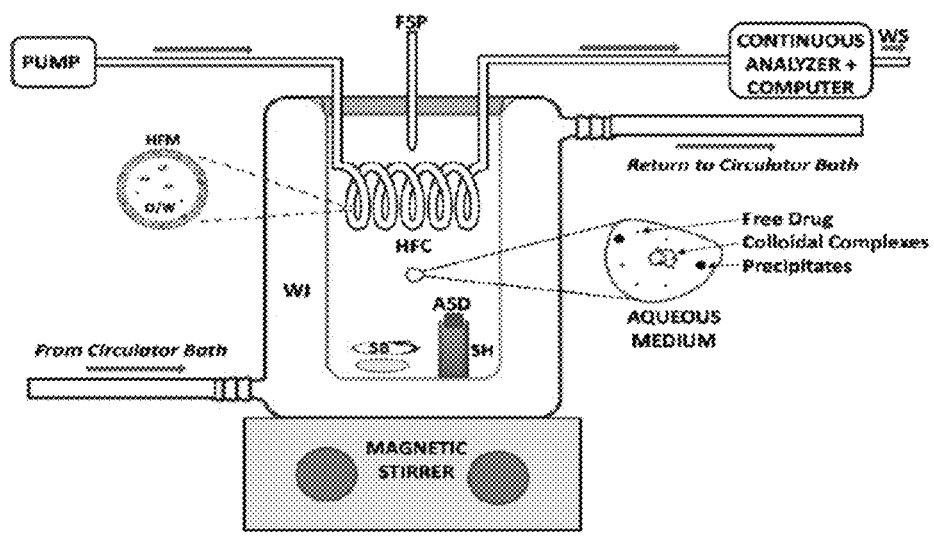
FIG. 1 shows an artificial gut simulator according to an example of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

A large fraction of drugs and drug candidates are of low to poor thermodynamic, and are classified as BCS Class II and Class IV compounds. Since poor solubility limits ultimate absorption and bioavailability, there have been substantial efforts to enhance the apparent solubility of such molecules. Toward this end, dosage forms that release drug in a supersoluble or supersaturated state, where drug is released at concentrations exceeding thermodynamic solubility. Supersaturating solid dosage forms (SSDFs) include high energy polymorphs, amorphous solids, pharmaceutical salts, and amorphous solid dispersions (ASDs). At supersaturated concentrations, drug absorption rate and extent are increased relative to the case where drug is released in the GI tract at or below saturation. However, amorphous-to-crystalline and polymorphic phase transformations can also occur, partially cancelling the intended benefit of the dosage form. Also, once dissolved, some of the supersaturated drug may precipitate.

Presently, the most common means to assess the performance of solid dosage forms, including SSDFs, is the standard United States Pharmacopeia (USP) dissolution test, with periodic withdrawal and analysis of liquid aliquots. Drug precipitates are excluded, and a "spring-parachute" dissolution profile is often observed, with the "spring" corresponding to rapid dissolution of drug into the supersaturated state, followed by the "parachute" during which some of the drug precipitates. After the "spring-parachute," the assayed concentration of drug may take on a plateau value, which may still be many fold higher than its value at saturation. The "quality" or "efficiency" of an SSDF is typically assessed by the area under the dissolution curve. Interestingly, the plateau can be sustained for many hours, suggesting that drug remains in its supersaturated, highly bioavailable state.

The standard USP dissolution test is neither optimal nor satisfactory for determining the efficacy of SSDFs, for two reasons. First, the system is closed with respect to the released drug, and any effects of drug absorption, which will tend to lower drug concentration in the intestinal fluid and hence reduce the rate of precipitation, are suppressed. In this sense, the standard dissolution test may be more stringent than necessary, underestimating efficacy, especially for BCS-II drugs which, by definition, have good intestinal permeability properties. Second, analytical techniques (e.g. HPLC) usually do not distinguish between free drug and nano-sized drug aggregates or drug that is complexed to the excipient polymers. While free drug is available for intestinal absorption, nano-aggregated or complexed drug probably is not. The analytical technique may significantly overestimate the ability of an SSDF to provide drug in a supersaturated, highly bioavailable form.

The overall goal is to develop a novel, holistic method for dissolution testing of SSDFs. We will construct a device that simulates absorption occurring simultaneously with dissolution. Such a device will be a superior tool for formulation screening.

FIG. 1 is a schematic of the Artificial Gut Simulator (AGS). A water-jacketed (WJ) beaker is connected to a temperature-controlled circulator bath, and sits on top of a MAGNETIC STIRRER, which drives rotation of stir bar (SB), mixing the aqueous contents inside the beaker, which may be a simple buffer or specialty solutions such as fasted state simulated intestinal fluid (FaSSIF) or simulated gastric fluid (SGF). The beaker contains a sample holder (SH) into which the SSDF is placed. (Variations might involve a bag suspended from the top, or freely "swimming" SSDF particles). The SSDF dissolves and releases its components (drug and admixed polymer), into the AQUEOUS MEDIUM as either free drug (small dots), colloidal complexes of drug with the admixed polymer (coils with associated small dots), or crystalline or amorphous precipitates (filled circles). Contents of the aqueous fluid can be monitored sporadically through a fluid sampling port (FSP).

A second fluid stream, originating in a syringe pump (PUMP), flows past a membrane, for example, through a hollow fiber coil (HFC), into a CONTINUOUS ANALYZER (usually a UV detector at fixed wavelength), which sends data to a COMPUTER for later processing. A waste stream (WS) may or may not be collected for further analysis. A cross section of the HFC is magnified in the figure. The HFC's lumen communicates with the aqueous fluid through an asymmetric hollow fiber membrane (HFM) that is favorable to free drug permeation, but is essentially impermeable to the other aqueous contents of the beaker, including salts, drug precipitates, and colloidally associated drug. (The latter, however, exchanges with free drug near the membrane.) An oil-in-water emulsion (O/W) flows through the HFC's lumen, concentrating drug in the oil droplets and increasing removal rate of drug. (Note: in FIG. 2 the SSDF is an ASD, and the non-free drug is represented as the colloidal complex with polymer. For the other SSDFs, the colloidal complexes can be replaced by nanocrystals or amorphous nanoparticles.) See Appendix for a detailed theory of operation.

In one example, the controlled removal of free drug by the coiled membrane mimics the absorptive surface of the small intestine. The contents of the beaker represent the intestinal lumen, the hollow fiber membrane represents the enterocytes lining the gut, and the lumen of the hollow fiber represents the mesenteric blood vessels. When the aqueous medium inside the beaker but outside the coil is well stirred, "drug absorption" should proceed at rate proportional to the free drug concentration.

The AGS may have significant flexibility in simulating complex processes. The aqueous medium in the beaker could contain a simple buffer, or it could contain lipids and bile salts. Other food-like elements could also be added. The fluid sampling port (FSP) might be used to add various components on a time dependent basis. Passage of the SSDF from the stomach to the small intestine could be modeled by starting off with an acidic aqueous medium in the beaker. At a selected time, a strong buffer can be added to reset pH to a desired value, and the absorption rate constant can be altered by changing flow rate through the HFC, or by switching the suspension that feeds the HFC. Alternatively, two AGSs in series could represent the stomach/duodenum.

In one example, magnetic stirring provides a uniform dispersion of all diffusible components in the aqueous medium. Free drug concentration is made available by dissolution, and is removed either by the HFC or by precipitation. Meanwhile, there may be exchange between free drug and colloidal complexes.

Removal of drug by HFC, which mimics absorption in vivo, is characterized by a rate constant, $k_a^{sim}$, where the superscript sim signals that this is a simulated rate constant, in contrast to rate constants measured in vivo. This rate constant will be quotient of the clearance of drug from the beaker through the HFC, $CL^{sim}$ and the volume of the aqueous fluid volume inside the beaker, V. We now present a model that predicts $CL^{sim}$ and therefore $k_a^{sim}$ based on HFC parameters, namely its length in contact with aqueous fluid in the beaker, L, the radius of its lumen, a, the rate of flow of the o/w emulsion through the lumen, Q, the permeability coefficient, P, of drug through the hollow fiber membrane, the volume fraction of oil droplets in the luminal emulsion, $\varphi_{o/w}$, and the drug's oil/water partition coefficient, $K_{o/w}$. In this model, the coil is taken to be straight, which is justifiable since the hollow fiber radius are much smaller than the coiling radius. The model geometry and parameters are diagrammed in FIG. 2, below.

Figure 2:
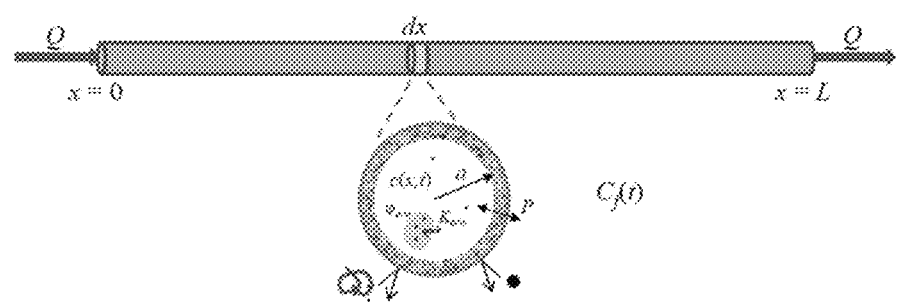
FIG. 2 shows a simplified straight section of a membrane component of an artificial gut simulator according to an example of the invention.

FIG. 2 shows a schematic illustrating processes and parameters used in model for removal of drug by HFC. Notice that free drug permeates through the hollow fiber membrane, but polymer-associated and precipitated drug are not.

Because the aqueous contents of the beaker are well stirred, concentration of free drug in the beaker is uniform at any time, and is designated $C_f(t)$. Since the fiber diameter is very narrow (a<<L), we may assume that intraluminal concentration across a radial cross section at any position x is also uniform. The aqueous free drug concentration in the lumen is designated c(x,t). The total intraluminal drug concentration, including both the water and oil phases, is given by $\omega c(x,t)$, where $\omega = 1+(K_{o/w}-1)\phi_{o/w}$. The mass balance for c(x,t) is $$\pi a^2 \omega \frac{\partial c}{\partial t} = -Q\omega \frac{\partial c}{\partial x} + 2\pi a P[C_f(t) - c(x, t)] \quad (1)$$

This expression assumes that only advection affects axial transport. Axial diffusion is ignored, since its contribution is very small inasmuch as the fiber is long compared to a typical "diffusion distance", $\sqrt{2Dt_{res}}$ that will be traversed over the residence time $t_{res}=L/(Q/\pi a^2)$ of fluid inside the fiber lumen. (This is equivalent to asserting that the Peclet number inside the fiber is large.) This last term can therefore be dropped. It can also be shown that drug concentration outside the fiber varies slowly compared to the rate at which the intraluminal contents achieve steady state, so we may assume a quasisteady state concentration profile ĉ(x, t), where $$0 = -Q\omega \frac{\partial \hat{c}}{\partial x} + 2\pi a P[C_f(t) - \hat{c}(x, t)] \quad (2)$$

with solution $$\hat{c}(x,t) = C_f(t)[1-\exp(-2\pi a P x/\omega Q)] \quad (3)$$

The rate of drug elution from the fiber at x=L is E(t)=ωQĉ (L,t). With these relations, and the definitions of clearance and elimination rate constant, we obtain $$CL^{sim}=E(t)/C_f(t)=\omega Q[1-\exp(-2\pi a PL/\omega Q)] \quad (4)$$

and then $k_a^{sim}=CL_{sim}/V$. The latter parameter, which is of ultimate interest, is therefore readily adjusted by judicious selection of V, Q, a, L, P, $\varphi_{o/w}$ and $K_{o/w}$.

Estimation of Parameters.

The parameters V, Q, L, and $\varphi_{o/w}$ are directly controlled by the designer. V is the volume of aqueous fluid in the beaker, Q is set by the pump, L is the length of the HFC that is submerged in the beaker fluid, and $\varphi_{o/w}$ is determined by the amount of oil and aqueous fluid that is loaded into the syringe pump. Hollow fiber tubing will be extracted from commercial hemodialyzers. A number of candidates will be tested, including hollow fibers based on cuprophane and polysulfone. The radius of tubing, a, can be determined either from product specifications, microscopic examination of cross section, or by residence time of a tracer dye. To determine permeability, P, saturated aqueous drug solutions will be introduced into several segments of tubing of equal length, L, which will then be crimped at the ends. The tubing segments will be placed in an excess of aqueous medium with vigorous stirring. At various times, t, segments will be removed and the intraluminal concentration of remaining drug will be determined by HPLC. An estimate for P will obtained by fitting the concentration time series to c(t)=c(0) exp(−2PLt/a). We do not expect to see, but will check for, a significant time lag in achieving this exponential decay. Such a lag, if present, will be incorporated into a slightly more complex model accounting for diffusion across the tubing wall.

The partition coefficient, $K_{o/w}$, can be predicted based on the octanol/water partition coefficient for the drug (obtained from the ClogP data base), and the predicted partition coefficient of drug between octanol and the chosen oil phase, based on the Hildebrandt equation. This technique is useful in making predictions and selecting candidate oil phases, but the actual value of $K_{o/w}$ will be determined experimentally by standard methods. In selecting the oil, care must be taken that it will not leak across the hollow fiber membrane into the beaker aqueous fluid. (Such leakage is unlikely when BSA is used in place of an oil in the luminal fluid.)

The parameter estimates obtained above will be used to predict $CL^{sim}$ and $k_a^{sim}$. However, ultimate validation will be obtained by running a length L of fiber through an excess of aqueous buffer, pumping the chosen aqueous/oil suspension with a specified aqueous drug concentration, $c_{in}$, at flow rate Q, and measuring eluted aqueous concentration, $c_{out}$. The ratio $c_{out}/c_{in}$ will rise from zero to a steady state value, $\bar{F}$, and the true value of $CL^{sim}$ will be determined as $CL^{sim}=Q\bar{F}$. Comparing this expression with the prediction of Eq. (4), with parameters estimated as above, will constitute model validation. Furthermore, by comparing the time required for $c_{out}/c_{in}$ to reach its steady state value $\bar{F}$, with $1/k_a^{sim}$, we can determine the validity of the quasi-steady state assumption used in Eqs. (2)-(4).

As might be expected with any dissolution testing system, homogeneity of contents of the aqueous fluid inside the beaker must be checked. There are several ways to accomplish this. Once a configuration [positions of sample holder and coils, size of stir bar, stirring rate (determined by strobe), etc.] is set, we will turn on stirring and at a designated time, t=0, we will inject blue dextran through the HFC port. This dye will not penetrate into the HFC. At selected later times, we will collect aliquots at various points in the center, near surfaces, and at corners of the beaker, and near the coil and compare dye concentrations. While we expect to see transient differences in concentrations taken from different points, these concentrations should equilibrate. In place of the dye we can introduce neutral buoyant, colored beads and track their movements with a high speed camera, and then process the data using particle tracking software. We can do the same with beads of increasing density or differing size to check how they drag at the bottom, and whether they accumulate in "backwaters." Finally, we can guide a fiber optic bundle into the vicinity of the HFC, in order to image hydrodynamic boundary layers. During this phase, a "dummy SSDF," e.g. a plastic tablet will be placed in the sample holder to assure that the geometric and hydrodynamic properties are preserved.

It may also be necessary to obtain precise knowledge of the delay between exit of intraluminal fluid from the beaker aqueous and the detector. This can be determined by pumping aqueous fluid containing dilute blue dextran though a fixed length of tubing with fixed rate Q, taking the difference between exit and entry times, and then scaling according to the length of tubing connecting the beaker aqueous and the detector.

Preliminary Tests of Apparatus.

Since in the present examples we wish to simulate absorption of drug in the small intestine, we will utilize fasted state simulated intestinal fluid (FaSSIF) in all our experiments. In the first test, indomethacin (IND), which we have selected as our model API, will be introduced into the beaker FaSSIF, below its solubility. To do this, IND will be dissolved in a small volume of ethanol (a good solvent of IND [x]), and this relatively concentrated solution will be injected into the FaSSIF residing in the beaker. The IND/ethanol solution volume will be very small compared to that of the FaSSIF, and both components will dissolve into the well stirred FaSSIF. The ethanol concentration will be small enough so as not to affect the solubility of IM in water. Just before injection, the PUMP will be turned on, initiating flow of intraluminal fluid as described above, $k_a$ will be determined by monitoring the exponential decay rate of concentration of IND flowing through the CONTINUOUS ANALYZER (UV, $\lambda$=295 nm).

An alternative estimate of $k_a$ will be obtained by direct measurement of IND concentrations inside the beaker. The predicted effects of V, Q, L, $\varphi_{o/w}$, and $K_{o/w}$ will be tested during this stage. Again, a "dummy ASD," will be placed in the sample holder.

It may also be necessary to monitor critical properties of the FaSSIF, especially pH, as a function of time. If soluble FaSSIF species such as buffers are lost into the HFC, they may need to be replenished periodically. Alternatively, an oil-in-FaSSIF emulsion will be chosen as the intraluminal fluid.

In the next, more interesting experiments, drug will be introduced into the FaSSIF above its saturation concentration. Again, drug will be introduced in ethanolic solution, but now the total drug injected will exceed its thermodynamic capacity to dissolve in FaSSIF. However, we can expect extended durations of supersaturation, which will depend on the rate of drug input, R(t). Here we define the time dependent degree of supersaturation as $S(t)=C_f(t)/C_{sat}$, where $C_{sat}$ is the drug's solubility in FaSSIF. Drug is subsaturated, saturated, and supersaturated, when S (t) is less than, equal to, or greater than 1, respectively.

When drug is administered in this way, we may write mass balance equation for drug according to $$\frac{dC_f}{dt} = \frac{R(t)}{V} - P(t) - k_a^{sim}C_f \qquad (5)$$

where P(t) is the rate of precipitation, which will eventually occur when drug is supersaturated.

Finally, in one example, the same procedures as were described in the above paragraph are performed, except with the pump turned on. Now we continuously monitor absorption of drug into the HFC and hence depletion of drug from the beaker. In this case, we should not expect an exponential decay of drug concentration throughout the study, since precipitated drug will not be available for absorption. Subtracting the measured rate of absorption from the rate of absorption that would be expected in the absence of precipitation, we obtain the time dependent rate of precipitation, P(t). Integrating this function from times 0 to t, we obtain the fraction of drug that has precipitated. We can, as before, also perform periodic assays of the FaSSIF in the AGS to check our results.

The data gathered in the last procedure places us in a position to evaluate how a degree of precipitation is affected by the absorption rate, $k_a$. Anticipating bioavailability studies in the subsequent Aims, we generate plots of total drug absorbed as a function of $k_a^{sim}$, and given the different programs of delivery of drug in the FaSSIF. The immediate hypothesis is that for a given program, R(t), an increase in $k_a^{sim}$ will lead to an increase in fraction absorbed, and that this affect will be more salient with faster R(t) programs, or, as dubbed by S&L, higher rates of supersaturation generation.

All simulations, fittings, and validations will be programmed and carried out in Matlab.

Figure 3:
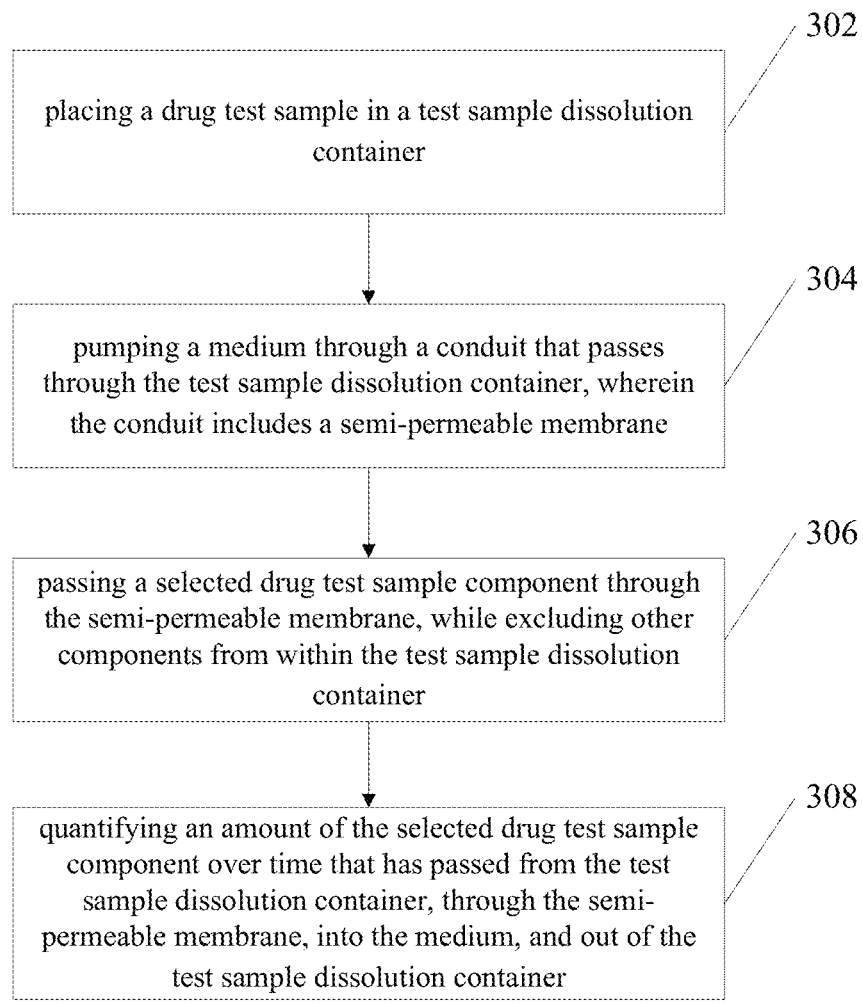
FIG. 3 shows a method of simulating a gut according to an example of the invention.

FIG. 3 shows an example method of drug dissolution testing according to one example. In operation 302, a drug test sample is placed in a test sample dissolution container. In operation 304, a medium is pumped through a conduit that passes through the test sample dissolution container, wherein the conduit includes a semi-permeable membrane. In operation 306, a selected drug test sample component passes through the semi-permeable membrane, while excluding other components from within the test sample dissolution container. In operation 308, an amount of the selected drug test sample component is quantified over time that has passed from the test sample dissolution container, through the semi-permeable membrane, into the medium, and out of the test sample dissolution container.

To better illustrate the method and apparatuses disclosed herein, a non-limiting list of examples is provided here:

Example 1 includes an artificial gut simulator including a test sample dissolution container, a conduit passing through the test sample dissolution container, the conduit including a semi-permeable membrane adapted to allow the transport of a selected test sample component through the semi-permeable membrane, while excluding other components from within the test sample dissolution container, a pump to drive an amount of medium through the conduit over time, and a detector to quantify an amount of the selected test sample component over time that has passed from the test sample dissolution container, through the semi-permeable membrane, and into the medium.

Example 2 includes the artificial gut simulator of example 1, wherein the selected test sample component includes a pharmaceutical drug.

Example 3 includes the artificial gut simulator of any one of examples 1-2, wherein the pharmaceutical drug includes a supersaturated solid dosage form pharmaceutical drug.

Example 4 includes the artificial gut simulator of any one of examples 1-3, further including a stirring device within the test sample dissolution container.

Example 5 includes the artificial gut simulator of any one of examples 1-4, further including a fluid sampling port to access the test sample dissolution container during testing.

Example 6 includes the artificial gut simulator of any one of examples 1-5, further including a fiber optic viewing device to monitor the test sample dissolution container during testing.

Example 7 includes the artificial gut simulator of any one of examples 1-6, wherein the semi-permeable membrane includes a hollow fiber coil.

Example 8 includes the artificial gut simulator of any one of examples 1-7, wherein the detector includes a continuous analyzer.

Example 9 includes the artificial gut simulator of any one of examples 1-8, wherein the continuous analyzer includes a UV detector.

Example 10 includes a method of drug dissolution testing. The method includes placing a drug test sample in a test sample dissolution container, pumping a medium through a conduit that passes through the test sample dissolution container, wherein the conduit includes a semi-permeable membrane, passing a selected drug test sample component through the semi-permeable membrane, while excluding other components from within the test sample dissolution container, and quantifying an amount of the selected drug test sample component over time that has passed from the test sample dissolution container, through the semi-permeable membrane, into the medium, and out of the test sample dissolution container.

Example 11 includes the method of example 10, wherein placing the drug test sample in the test sample dissolution container includes placing a supersaturated solid dosage form pharmaceutical drug sample in the test sample dissolution container.

Example 12 includes the method of any one of examples 10-11, wherein pumping the medium through the conduit includes pumping an oil-in-water emulsion through the conduit that passes through the test sample dissolution container.

Example 13 includes the method of any one of examples 10-12, further including placing lipids in the test sample dissolution container along with the drug test sample.

Example 14 includes the method of any one of examples 10-13, further including placing bile salts in the test sample dissolution container along with the drug test sample.

Example 15 includes the method of any one of examples 10-14, further including varying pH within the test sample dissolution container during testing.

Example 16 includes the method of any one of examples 10-15, further including adjusting an absorption rate constant by varying flow rate through the semi-permeable membrane.

Example 17 includes the method of any one of examples 10-16, further including stirring the test sample dissolution container during testing.

Example 18 includes the method of any one of examples 10-17, further including quantifying flow within the test sample dissolution container during testing by tracking particle movement with a camera, and processing the data using particle tracking software.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An artificial gut simulator, comprising:
a test sample dissolution container;
a stirring device within the test sample dissolution container;
a conduit passing through the test sample dissolution container, the conduit including a semi-permeable membrane adapted to allow the transport of a selected test sample component through the semi-permeable membrane, while excluding other components from within the test sample dissolution container;
a pump to drive an amount of medium through the conduit over time; and
a detector to quantify an amount of the selected test sample component over time that has passed from the test sample dissolution container, through the semi-permeable membrane, and into the medium.

2. The artificial gut simulator of claim 1, wherein the selected test sample component includes a pharmaceutical drug.

3. The artificial gut simulator of claim 1, wherein the pharmaceutical drug includes a supersaturated solid dosage form pharmaceutical drug.

4. The artificial gut simulator of claim 1, further including a fluid sampling port to access the test sample dissolution container during testing.

5. The artificial gut simulator of claim 1, further including a fiber optic viewing device to monitor the test sample dissolution container during testing.

6. The artificial gut simulator of claim 1, wherein the semi-permeable membrane includes a hollow fiber coil.

7. The artificial gut simulator of claim 1, wherein the detector includes a continuous analyzer.

8. The artificial gut simulator of claim 1, wherein the continuous analyzer includes a UV detector.

9. A method of drug dissolution testing, comprising:
placing a drug test sample in a test sample dissolution container;
pumping a medium through a conduit that passes through the test sample dissolution container, wherein the conduit includes a semi-permeable membrane;
passing a selected drug test sample component through the semi-permeable membrane, while excluding other components from within the test sample dissolution container; and
quantifying an amount of the selected drug test sample component over time that has passed from the test sample dissolution container, through the semi-permeable membrane, into the medium, and out of the test sample dissolution container.

10. The method of claim 9, wherein placing the drug test sample in the test sample dissolution container includes placing a supersaturated solid dosage form pharmaceutical drug sample in the test sample dissolution container.

11. The method of claim 9, wherein pumping the medium through the conduit includes pumping an oil-in-water emulsion through the conduit that passes through the test sample dissolution container.

12. The method of claim 9, further including placing lipids in the test sample dissolution container along with the drug test sample.

13. The method of claim 9, further including placing bile salts in the test sample dissolution container along with the drug test sample.

14. The method of claim 9, further including varying pH within the test sample dissolution container during testing.

15. The method of claim 9, further including adjusting an absorption rate constant by varying flow rate through the semi-permeable membrane.

16. The method of claim 9, further including stirring the test sample dissolution container during testing.

17. The method of claim 16, further including quantifying flow within the test sample dissolution container during testing by tracking particle movement with a camera, and processing the data using particle tracking software.

* * * * *